United States Patent [19]

Shamos

[11] Patent Number: 4,483,329

[45] Date of Patent: Nov. 20, 1984

[54] DEVICE AND METHOD FOR THE REDUCTION OF LUMBAR LORDOSIS

[76] Inventor: Desmond E. Shamos, 6565 Spencer Hwy., #2902, Pasadena, Tex. 77505

[21] Appl. No.: 523,849

[22] Filed: Aug. 17, 1983

Related U.S. Application Data

[63] Continuation of Ser. No. 305,176, Sep. 24, 1981, abandoned.

[51] Int. Cl.³ ............................................... A61F 5/00
[52] U.S. Cl. ..................................................... 128/69
[58] Field of Search ...................... 128/69, 68, 82, 83, 128/78

[56] References Cited

U.S. PATENT DOCUMENTS

| | | | |
|---|---|---|---|
| 712,375 | 10/1902 | Hartford | 128/69 |
| 1,497,837 | 6/1924 | Boehler | 128/69 |
| 1,833,426 | 11/1931 | Knudson | 128/69 |
| 2,343,204 | 2/1944 | Paton | 128/69 |
| 3,672,360 | 6/1972 | Langhammer | 128/69 |
| 4,230,099 | 10/1980 | Richardson | 128/69 |

*Primary Examiner*—John D. Yasko
*Attorney, Agent, or Firm*—Arnold, White & Durkee

[57] ABSTRACT

A device for reducing lumbar lordosis. The device is shaped to fit the sacral area of a supine patient to provide support for the apex of the sacrum of such a supine patient. The body weight of such a supine patient will then have the effect of biasing the sacrum to reduce lumbar lordosis and thereby alleviate low backache.

9 Claims, 8 Drawing Figures

DEVICE AND METHOD FOR THE REDUCTION OF LUMBAR LORDOSIS

This is a continuation of application, Ser. No. 305,176, filed Sept. 24, 1981 now abandoned.

This invention relates to a device for and to a method for reducing lumbar lordosis.

Many people suffer from low backache or backache in the lumbar region of the spine. This can be attributable to bad posture or to an excess of weight in the stomach area. Overweight people and pregnant women frequently have backache in the lumbar region. The backache results from lumbar lordosis caused by the unbalanced weight distribution pulling the lumbar region of the spine in the anterior direction. This causes an increase in the lumbosacral angle, and is accompanied by pivotal movement of the sacrum for the sacral base to move anteriorly and for the apex of the sacrum to move posteriorly.

Low backache can be relieved by reducing the degree of lumbar lordosis. This can be done by manipulating the sacral area to restore the lumbar region of the spine and the sacrum to their proper attitudes and positions. Normally, such manipulation is done by trained therapists or trained practitioners.

It is one object of this invention to provide a device and method for reducing lumbar lordosis.

According to the invention there is provided a device for reducing lumbar lordosis, the device being shaped to fit the sacral area of a supine patient to provide support for the apex zone of the sacrum of such a supine patient for the patient's body weight to bias the sacrum to reduce lumbar lordosis.

The device conveniently includes a base surface to support the device on a supporting surface, and an upper surface to be directed upwardly during use, the upper surface being shaped to support the apex zone of a sacrum during use.

The upper surface is conveniently curved to match the curvature of the apex zone of an average sacrum. Preferably, the upper surface would be curved to be complementary to the curvature of the apex of such an average sacrum.

The device has a trailing end to be directed towards the head of a patient during use, and an opposed leading end to be directed towards the feet of a patient during use.

In the presently preferred embodiment of the invention, the upper surface will diverge away from the base surface from the trailing end to a peak at the leading end of the device so that, in side elevation, the device will be of wedge configuration.

In the preferred embodiment of the invention the upper surface of the device will be curved along its length from the trailing end of the device to its peak to be complementary to the curvature of the apex of an average sacrum.

It will be appreciated that sacrums vary in size and shape and therefore have apex curvatures which vary.

In practice the upper surface of the device can be shaped to that it will be substantially complementary to or will substantially match the curvature of a major proportion of sacrum apexes, and devices can be specifically shaped for undersized sacrums or for sacrums which have unusually greater or unusually smaller curvature along the apex.

The upper surface may conveniently diverge relatively to the base surface to provide the upper surface at an inclination corresponding generally with the inclination which an average sacrum apex should have for a proper lumbar profile when a patient is resting supine on a surface on which the base of the device is supported. Use of the device will therefore tend to correct the position of the sacrum and thus of the lumbar region of the spine of a patient.

It will be appreciated, however, that the curvature may be exaggerated so that it will tend to pivotally displace the sacrum into an over-corrected condition to exaggerate the reduction of lumbar lordosis, thereby ensuring that lumbar lordosis will be alleviated an appropriate amount when the bias effect of the device is removed.

The device may include a recess for accommodating the spinous process of a patient thereby avoiding any pressure being exerted on the spinous process during use.

The device may, in an embodiment of the invention, have an enlarged base plate defining the base surface on one side thereof and a support surface on the opposed side thereof. In this embodiment the recess for receiving the spinous process may be in the form of an elongated recess in the support surface of the base plate, thereby allowing the support surface on opposed sides of the recess to support the pelvis of a supine patient.

The device may conveniently be adjustable in height to allow adjustment of the inclination of the upper surface relatively to a support surface on which the device is supported. This allows the inclination of the upper surface to be adjusted for the comfort of a patient using the device in relation to the particular inclination of the apex of the sacrum of such a patient.

The device may be adjustable by any appropriate inclination adjustment means which would be known to a person of ordinary skill in the art.

Thus, for example, the device may be provided with extendable legs, with an adjustment bar which is displaceable between the leading and trailing ends of the device, by a plurality of legs which are displaceable between operative and inoperative condition, or the like. In an alternative embodiment of the invention, the upper surface may be provided on a wedge member which is located on a base plate, with the wedge member being pivotally displaceable on the wedge plate to alter the inclination of the upper surface. In one example of this embodiment of the invention, the wedge device may have a curved lower surface which is curved along its length. The base plate may have a complementarily curved recess and mating locking formations may be provided at spaced intervals along the complementary surfaces to allow the wedge part to be located in a desired inclination on the base plate.

The invention further extend to a method of reducing lumbar lordosis in a patient, the method comprising causing a patient to lie supine on a surface, and positioning a support device in the sacral area of the patient to support the apex of the patient's sacrum for the patient's body weight to displace the sacral base posteriorly to thereby reduce lumbar lordosis.

The device of this invention may be made of any suitable material. Thus, for example, it may be made out of a synthetic plastics material, out of wood, out of rubber or synthetic rubber, out of a metal alloy, or out of a combination of these materials.

The device may be formed as a one-piece device or may be formed as two separate pieces which are clipped or otherwise joined together.

Embodiments of the invention are now described by way of example with reference to the accompanying drawings.

Figure 1:
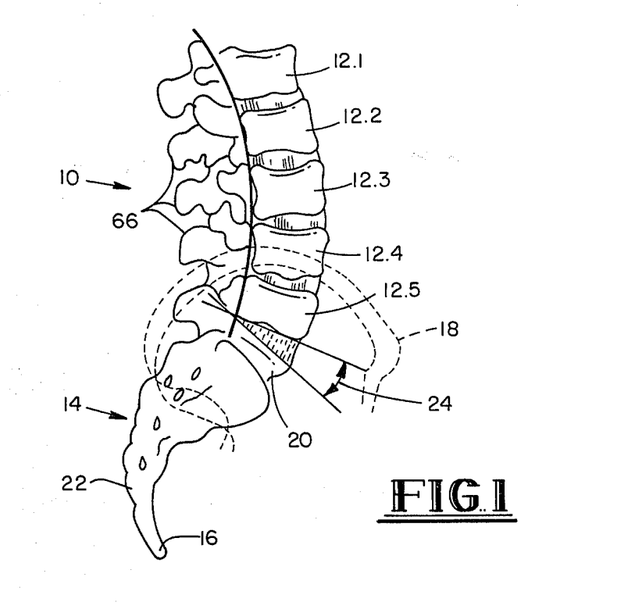
FIG. 1 shows a schematic, fragmentary, side elevation of the lumbar area of a typical spine exhibiting a degree of lumbar lordosis.
Figure 2:
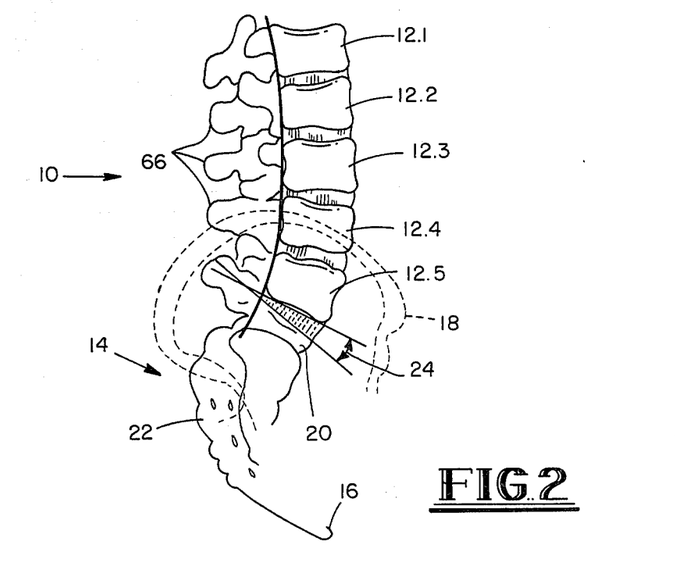
FIG. 2 shows a views similar to that of FIG. 1 after reduction or alleviation of the lumbar lordosis in the spine of FIG. 1.

With reference to FIGS. 1 and 2 of the drawings, reference numeral 10 refers generally to the lumbar region of a spine comprising the first, second, third, fourth and fifth lumbar vertebrae 12.1 to 12.5 respectively, the sacrum 14, the coccyx 16 and the iliac 18. The sacrum 14 has an apex indicated by numeral 22.

The lumbar region 10 in FIG. 1 is shown exhibiting lumbar lordosis in a male patient as would typically be caused by excess weight in the stomach area. The lumbar region 10 in FIG. 1 exhibits a lumbosacral angle (identified by numeral 24) of about 14° between the fifth lumbar vertebrae 12.5 and the base 20 of the sacrum 14.

In FIG. 2 of the drawings the lumbar region 10 is shown after alleviation of the lumbar lordosis. It will be noted that the lumbosacral angle 24 has been reduced by about 1° to about 13°.

This reduction of lumbar lordosis results from pivotal displacement of the sacrum 14 so that the base 20 of the sacrum moves posteriorly while the apex 22 moves anteriorly thereby forcing the lumbar region 10 to become more linear.

It will be appreciated that the lumbar region 10 illustrated in the drawings has been exaggerated to illustrate the condition and the reduction thereof. It must be appreciated that the lumbar curve is more pronounced in females than in males and that curvatures vary over a limited range from case to case. Generally, however, reduction of the lumbosacral angle by about 1° will tend to reduce lumbar lordosis sufficiently to alleviate or even totally eliminate low backache.

Figure 3:
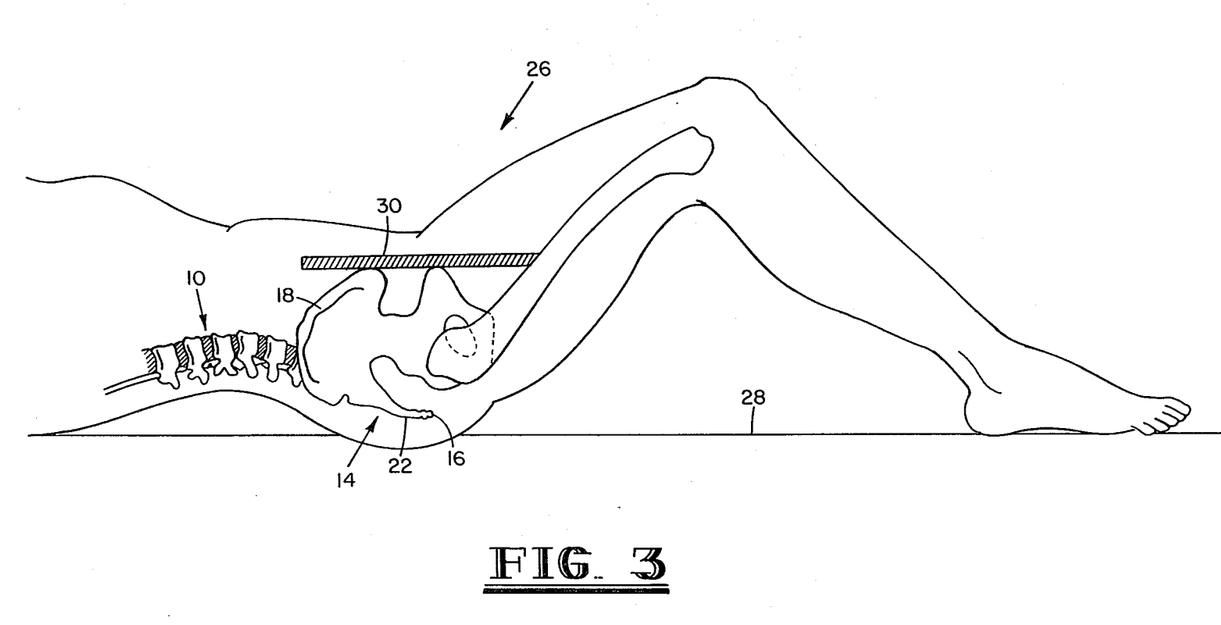
FIG. 3 shows a fragmentary, schematic side elevation of a patient with lumbar lordosis, resting in a supine position on a surface.
Figure 4:
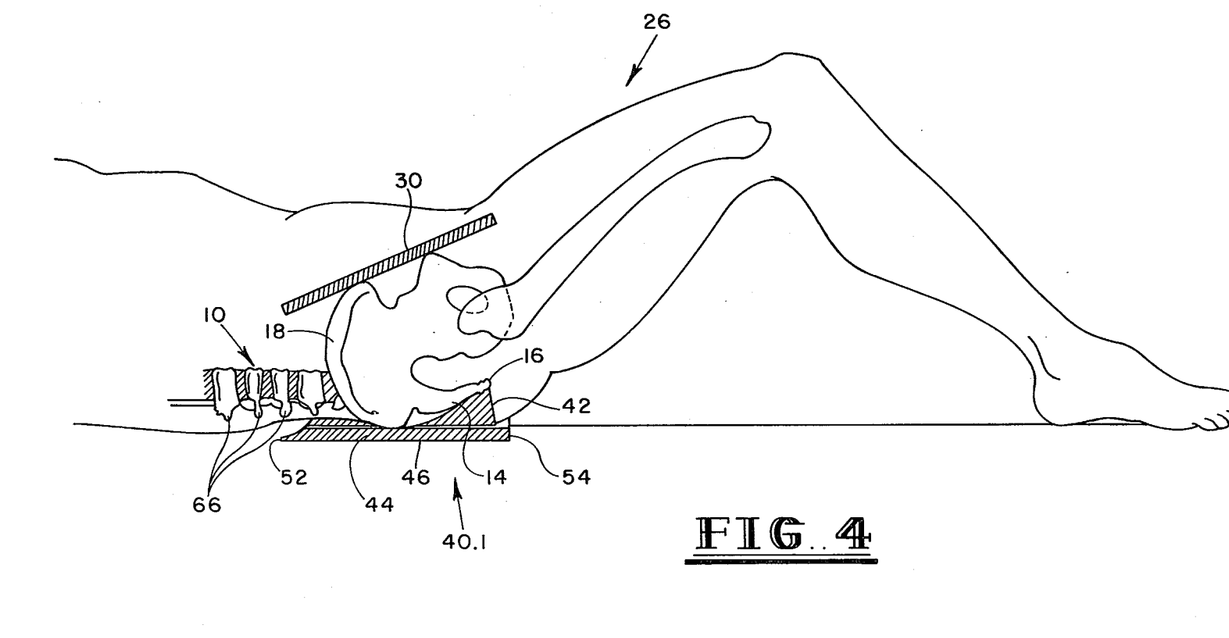
FIG. 4 shows a view similar to that of FIG. 3 with a device in accordance with this invention in its operative position to thereby reduce lumbar lordosis.

With specific reference to FIGS. 3 and 4 of the drawings, reference numeral 26 refers generally to a patient resting supine on a resting surface 28.

In FIG. 3 of the drawings the lumbar region 10 corresponds to that illustrated in FIG. 1. The patient 26 is therefore, in FIG. 3 of the drawings, exhibiting a sufficient degree of lumbar lordosis to produce distressing low backache.

A marking plate 30 has been drawn in in both FIGS. 3 and 4 to indicate the variation in the position of the pelvis and iliac 18 after treatment in accordance with this invention.

FIG. 4 shows a view similar to that of FIG. 3, but in which the patient 26 is resting on one embodiment of a device 40.1 in accordance with this invention for reducing lumbar lordosis. The device 40.1 is illustrated in subsequent figures of the drawings.

It will be noted when comparing FIGS. 3 and 4 of the drawings that the marking plate 30 exhibits a substantially different angle relatively to the resting surface 28 in FIG. 4 than it does in FIG. 3. This, while exaggerated, demonstrates the manner in which the device 40.1 has pivotally displaced the sacrum 14 of the patient 26 to move the base 20 of the sacrum in the posterior direction, while moving the apex 22 of the sacrum in the anterior direction. This causes the lumbar region 10 to straighten until it is virtually linear and parallel to the resting surface 28 as shown in FIG. 4.

It must be appreciated that the lordosis in FIG. 3 has been exaggerated, as has the reduction in lumbar lordosis illustrated in FIG. 4. This has been done to clearly demonstrate the problem and the manner in which the device 40.1 in accordance with this invention can eliminate or allevaite the problem.

From x-ray analyses of experiments performed by the applicant, applicant has found that a one-degree reduction in the lumbosacral angle 24 generally reduces lumbar lordosis sufficiently to alleviate (and usually totally eliminate) low backache in an average patient.

Figure 5:
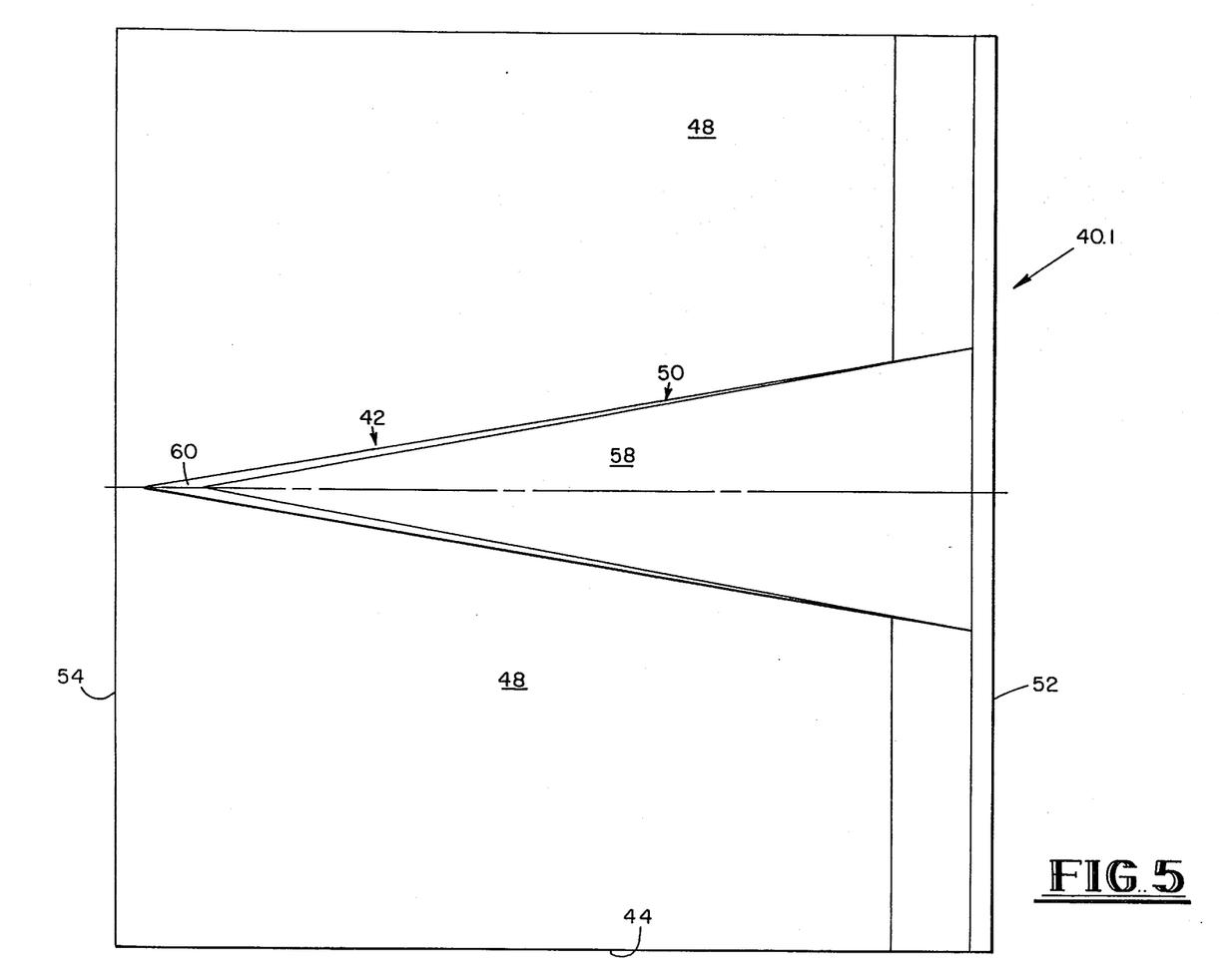
FIG. 5 shows a plan view of one embodiment of a device in accordance with this invention.
Figure 6:
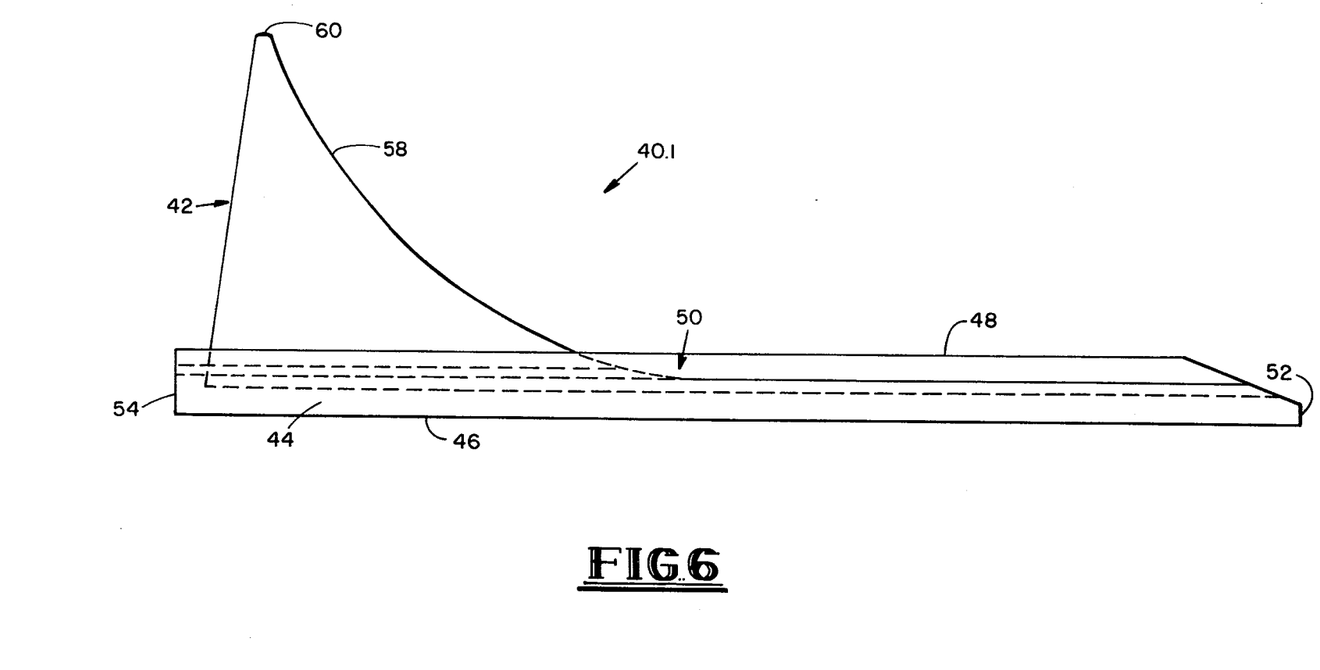
FIGS. 6 and 7 show a side view and an end view respectively of the device of FIG. 5.
Figure 7:
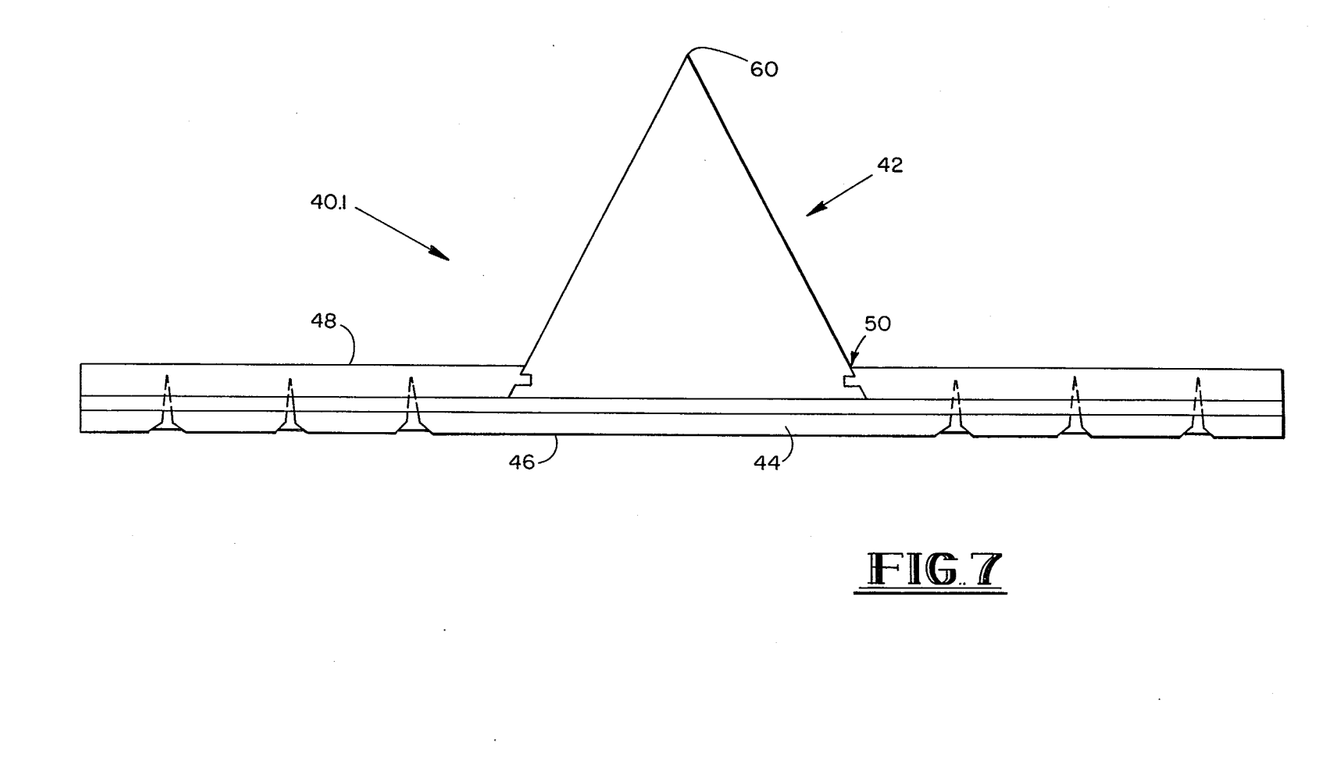

The device 40.1 of FIG. 4 is illustrated in detail in FIGS. 5 to 7 of the drawings. Therefore, with reference to FIGS. 4 to 7 of the drawings, it will be noted that the device 40.1 is shaped to fit the sacral area of a supine patient 26 between the rear pelvic area of the patient 26 and a resting surface 28 on which the patient is resting in a supine condition.

The device 40.1 comprises a wedge member 42 and a base plate 44.

The base plate 44 defines a base surface 46 on which the device 40.1 is supported on a surface such as the resting surface 28.

The base plate 44 further defines a support surface 48 on the opposed side to the base surface 46 for supporting the pelvic area of the patient 26 when using the device 40.1.

The base plate 44 has an elongated recess 50 provided therein. The recess 50 extends from a trailing end 52 of the base plate 44 to a leading end 54 thereof.

When the device 40.1 is in use, the trailing end 52 is directed towards the head of the patient 26, while the leading end 54 is directed towards the feet of the patient 26 (as shown in FIG. 4).

In FIGS. 4 to 7 of the drawings, the recess 50 serves a dual purpose.

One purpose of the recess 50 is to allow the wedge member 42 to be removably engaged with the base plate 44. The recess 50 is therefore of triangular shape in plan view while the wedge member 42 is of complementary triangular shape in plan view. The wedge member 42 can therefore be displaced along the recess 50 in a direction from the trailing end 52 to the leading end 54 until it jams in position in the recess 50. As shown in FIG. 7 of the drawings, complementary tongue and groove formations are provided for positively locating the wedge member 42 in position on the base place 44.

The wedge member 42 has an upper surface 58 to be directed upwardly during use.

The wedge member 42 has the upper surface 58 curved to diverge away from the base surface 46 from the direction of the trailing end 52 of the base plate 44 to a peak 60 adjacent the leading end 54 of the base plate 44.

The upper surface 58 is smoothly curved to be generally complementary to the curvature of the apex 22 of the sacrum 14. The upper surface 58 is curved, however, so that its degree of curvature relatively to the base surface 46 is steeper than the degree of curvature which the apex 22 of the sacrum 14 should have relatively to a resting surface 28 for an average patient 26 without lumbar lordosis.

This increased inclination will ensure that, as is hereinafter described, when a patient 26 uses the device 40.1, the device 40.1 will bias the sacrum 14 into an over-corrected position. This insures that when the device is removed, the sacrum 14 will return slightly and the lumbar region 10 will no longer be in an over-corrected position, but in a position where lumbar lordosis has been reduced sufficiently to eliminate low backache.

The wedge member 42 is thus substantially of wedge shape in side elevation (as shown in FIG. 6). It is also substantially of wedge configuration in plan view to insure a proper and confortable fit with the sacral area of a patient such as the patient 26.

In use, a patient suffering from low backache as a result of lumbar lordosis will lie in a supine position on the resting surface 28.

The patient will then flex both legs and hips as shown in FIG. 3.

The patient will thereafter carefully place the device 40.1 in position under the pelvic area of the patient with the apex 20 of the sacrum 14 in close contact with the upper surface 58 of the wedge member 42 as shown in FIG. 4. The patient 26 should position the device 40.1 for the greatest degree of comfort.

In this position, with the apex 22 of the sacrum 14 bearing against and supported by the upper surface 58, the spinous process 66 is freely accommodated within the recess 50 thereby avoiding any pressure on the spinous process 66. In other words, the pelvis of the patient 26 is supported on the support surface 48 on opposed sides of the recess 50 without any pressure on the spinous process 66.

With the apex 22 of the sacrum 14 supported on the arcuate upper surface 58 of the wedge member 42, the weight of the patient 26 will cause the sacrum 14 to pivot with the apex 22 being displaced in the anterior direction while the base 20 will be displaced in the posterior direction. This pivotal displacement of the sacrum 14 will force the lumbar region 10 to straighten thereby reducing the degree of lumbar lordosis and thereby eliminating or at least substantially alleviating low backache.

As shown in FIGS. 1 and 2 of the drawings, the reduction of lumbar lordosis, resulting in a reduction of the lumbosacral angle of about 1° from, on the average, 14° to 13° will tend to eliminate lower backache entirely in an average case.

The inclination of the upper surface 58 may be adjusted by adjusting the inclination of the base plate 44 relatively to the resting surface 28 to accommodate the sacral inclination of a patient 26 thereby improving the individual's comfort and improving the extent to which lumbar lordosis is alleviated. The inclination of the base plate 44 relatively to the resting surface 28 may be adjusted by placing a support device or the like between the base surface 46 and the resting surface 28.

The duration for which the device 40.1 is used by a particular patient 26 will depend upon the patient's own tolerance level. After a reasonable period of use, however, applicant has found that lumbar lordosis is generally relieved to a sufficient extent to substantially reduce and usually to often entirely eliminate low backache. The device may for example be used for several minutes or more.

Figure 8:
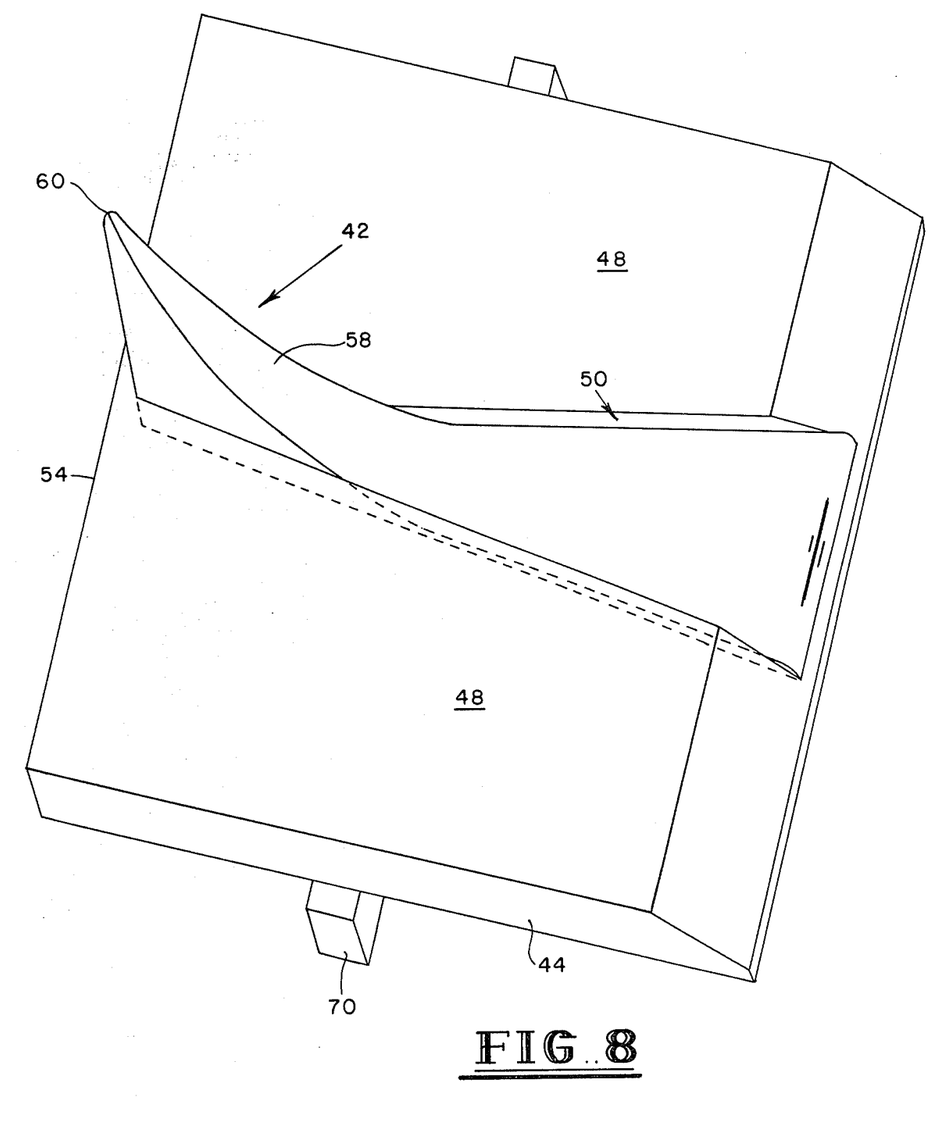
FIG. 8 shows a perspective view of an alternative embodiment of the device for reducing lumbar lordosis in accordance with this invention.

With reference to FIG. 8 of the drawings, reference numeral 40.2 refers generally to a device corresponding in most respects with the device 40.1. However, in FIG. 8 of the drawings, a height adjustment bar 70 is illustrated in position where it cooperates with the base plate 44.

The bar 70 is slidably attached to the base plate 44 for displacement along the base plate 44 between its leading and trailing ends 54 and 52 respectively. By displacing the bar 70 the inclination of the base plate 44 relatively to a resting surface 28 can be adjusted to suit the comfort of an individual patient.

The embodiment of the invention as illustrated in the drawing provides the advantage that a patient such as the patient 26 can use the device 40 as and when required in the comfort of the patient's own environment. The device can be inserted into position when required. In the correct position, the weight of the patient merely resting in a relaxed condition on the device will ensure that the device will bias the sacrum into a proper attitude to cause a reduction in lumbar lordosis and thereby alleviate or reduce low backache. Backache can thus be alleviated as and when required without the need to make a special visit to a therapist or other skilled practitioner.

This pivotal displacement of the sacrum 14 must take off pressure from the anterior longitudinal ligament which lies along the lumbar spine. Likewise, it will tend to redistribute pressure on the intervertebral disc and, by the same token, take pressure off the following ligamentous structures of the sacrum: the short posterior ligament; the anterior sacral ligament; the iliolumbar ligament; the sacrospinous ligament; the sacrotuberous ligament and the long posterior sacroiliac ligaments.

The net result of the use of a device as illustrated in the drawings, is therefore the alleviation of stress in the low back, including alleviation of stress in the sacrospinalis mass of muscles.

I claim:

1. A method of reducing lumbar lordosis in a patient, the method comprising causing a patient to lie supine on a surface, and positioning a support device in the sacral area of the patient to support the apex of the patient's sacrum without providing support for the base of the patient's sacrum for the patient's body weight to displace the sacral base posteriorly and to displace the apex anteriorly to reduce lumbar lordosis.

2. A device for reducing lumbar lordosis, the device comprising a wedge member having a base surface to support the device on a supporting surface, and having an upper surface to be directed upwardly during use, the upper surface being curved to generally match the curvature of the apex zone of an average sacrum, and the device being shaped to fit the sacral area of a supine patient for the upper surface to engage with and to provide support for the apex zone of the sacrum of such a supine patient without the wedge member providing support for the base of the sacrum for the patient's body weight to bias the sacrum to reduce lumbar lordosis.

3. A device according to claim 2, in which the upper surface is curved to be complementary to the curvature of the apex of an average sacrum.

4. A device, for reducing lumbar lordosis, the device comprising a wedge member having a base surface to support the device on a supporting surface, and having an upper surface to be directed upwardly during use, the device including a trailing end to be directed towards the head of a patient during use, and an opposed leading end, and having the upper surface diverging away from the base surface from the trailing end to a peak adjacent the leading end of the device, the upper surface being curved to be complementary to the curvature of the apex zone of an average sacrum, and the device being shaped to fit the sacral area of a supine patient for the upper surface to engage with and to provide support for the apex zone of the sacrum of such a supine patient for the patient's body weight to bias the sacrum to reduce lumbar lordosis.

5. A device according to claim 4, in which the upper surface diverges relatively to the base surface to provide the upper surface at an inclination corresponding generally with the inclination which an average sacrum apex should have for a proper lumbar profile when a patient is resting supine on a surface on which the base surface of the device is supported.

6. A device according to claim 5, in which the device has an enlarged base plate defining the base surface on one side thereof and a support surface on the opposed side thereof, and in which the support surface has an elongated recess for receiving the spinous process of a patient while supporting the pelvis of a supine patient on the support surface.

7. A device according to claim 6, which is adjustable to adjust the inclination of the upper surface relatively to the base surface.

8. A device according to claim 4, in which the device has two opposed sides which taper inwardly towards each other in the direction of the peak of the device.

9. A device according to claim 5, in which the upper surface is inclined to reduce the lumbo-sacral angle of a patient using the device, by about 1°.

* * * * *